United States Patent [19]

Dunshee et al.

[11] Patent Number: 4,837,062

[45] Date of Patent: Jun. 6, 1989

[54] PRESSURE-SENSITIVE ADHESIVE COATED SHEETS AND TAPE PAD WITH EASILY SEPARABLE TABS

[75] Inventors: Wayne K. Dunshee, Maplewood; Sydney B. Hames, Woodbury, both of Minn.

[73] Assignee: Minnesota Mining and Manufacturing Company, St. Paul, Minn.

[21] Appl. No.: 153,582

[22] Filed: Feb. 8, 1988

[51] Int. Cl.$^4$ ................................................ B32B 3/08
[52] U.S. Cl. ........................................ 428/41; 128/40; 128/77; 128/124; 128/126; 128/192; 128/194; 128/155; 206/484
[58] Field of Search ............... 428/40, 41, 77, 192, 428/354, 124, 126, 194; 128/155; 206/484, 813, 820

[56] References Cited

U.S. PATENT DOCUMENTS

| 2,248,317 | 7/1941 | Van Cleef | 428/40 X |
| 4,418,822 | 12/1983 | Dotta | 128/155 |
| 4,598,004 | 7/1986 | Heinecke | 428/40 |
| 4,614,183 | 9/1986 | McCracken et al. | 128/155 |
| 4,650,706 | 3/1987 | Emmel | 428/77 X |

FOREIGN PATENT DOCUMENTS 656328  8/1951  United Kingdom .................. 428/41

Primary Examiner—Alexander S. Thomas
Attorney, Agent, or Firm—Donald M. Sell; Walter N. Kirn; Dale A. Bjorkman

[57] ABSTRACT

A single, flexible, pressure-sensitive adhesive coated sheet having one or more co-terminal, V-fold liner tabs attached to portions of the adhesive coated surface; and tape pads formed from a plurality of such sheets. In this invention one leg of a V-shaped tab is adhered to the adhesive coated surface of the sheet. An unattached leg of the tab forms a handle which is easily grasped to facilitate manual separation of the tab from the sheet when it is adhered to a receptor surface.

14 Claims, 2 Drawing Sheets

PRESSURE-SENSITIVE ADHESIVE COATED SHEETS AND TAPE PAD WITH EASILY SEPARABLE TABS

BACKGROUND OF THE INVENTION

1. Technical Field

This invention relates to a pressure-sensitive adhesive coated sheet having at least one co-terminal, V-fold tab which facilitates application of the sheet to a receptor surface. The invention extends to a tape pad comprised of a plurality of such sheets with each sheet having a V-fold tab adhered thereto.

2. Background Art

The art is replete with descriptions of tape pads comprising a plurality of pressure-sensitive adhesive coated sheets adhered to each other.

U.S. Pat. No. 2,030,135 discloses adhesive units for the purpose of securing signs, pictures or displays onto walls, posts, sign boards and other supportive structures. Each adhesive unit has an adhesive-free edge to afford easier separation of the units.

U.S. Pat. No. 2,528,602 discloses a cleaning pad comprising sheets coated with an adhesive on one side such that the sheet may be used to remove lint, dust, hair and other objects from wearing apparel. Each cleaning sheet in the pad has a protective strip located along a side portion in order to facilitate the peeling of the cleaning sheet from the pad. The strip may be any suitable material that does not adhere to the pad (e.g., cellophane).

U.S. Pat. No. 2,574,152 discloses an adhesive tape package which is a stack of sheets with pressure-sensitive adhesive coated on one side and a non-tacky water soluble adhesive on the other side. The adhesive package may be preformed as mounting devices for mounting photos and may also be packaged in stacks and rolls for other uses. Every other sheet in the stack has a cutaway corner to facilitate the removal of one sheet from the next in the package.

U.S. Pat. No. 2,724,847 discloses a lint removing device comprising a pad of adhesive sheets wherein the individual sheets are pressed against a garment to remove lint. Each sheet has a strip on one edge to separate one edge of the sheet from the edge of the sheet located therebelow such that each sheet may be easily peeled from the pad.

U.S. Pat. No. 3,083,393 discloses a stack of adhesive sheets wherein each sheet is placed in a frame and thereafter used to clean the soles of shoes. A small, thin triangle of non-tacky material such as aluminum foil or cellophane is attached to a corner of each sheet in order to facilitate the separation of the sheets. Another method disclosed to facilitate separating each sheet is to leave the sheet corners adhesive-free.

U.S. Pat. No. 3,665,543 discloses a stack of sheets, with adhesive on both surfaces, to be used as a door mat to remove dirt particles from shoe soles. A pull tab is located on one corner of each sheet to facilitate the stripping and separation of one sheet from the remainder of the stack.

U.S. Pat. No. 3,785,102 discloses a stack of sheets with adhesive on both sides with each sheet to be used as a mat to remove dust and dirt from shoe soles. A corner area or portion of the upper surface of each sheet is free from adhesive for the purpose of separating one sheet from the rest of the stack.

U.S. Pat. No. 4,107,811 discloses a stack of peelable sheets with a layer of adhesive on the upper surface of each sheet. The stack is to be placed at the entrance of a room for the purpose of removing dirt and dust from the soles of shoes. A corner of each sheet is rendered non-tacky with a thin coating of non-adhesive material to facilitate the peeling of each sheet from the stack. The non-adhesive coating may be colored to indicate to the user which corner is to be peeled first.

U.S. Pat. No. 4,650,706 discloses a tabbed tape pad in which regressive, folded tabs provide a convenient handle and help distribute the forces applied during sheet separation. The tabs adhered to the pressure-sensitive adhesive side of the tape strip become increasingly shorter on each successive sheet from the top tape strip to the bottom tape strip of the pad. The free end of each tab is folded back upon itself to provide a removable tab end which is free from adhesive. This tab covered end affords facile removal of the tab during application of the full length of the tape strip to a receptor surface.

The tape pads described in these patents all include a means for facilitating manual separation of the sheets from the rest of the pad, such as an end portion of each sheet that is not coated with adhesive, or a portion having an overcoating or liner covering the adhesive enabling that portion of the sheet to be easily engaged with the fingers.

The presence of such uncoated, overcoated or linered portions described in the aforementioned patents usually presents no significant problems for the intended uses of the sheets (e.g., the removal of lint or debris). For other intended uses of such sheets, however, such as where the sheets are to be applied onto or over surfaces, the presence of such uncoated, overcoated or linered portions of the sheets can be undesirable as the entire sheet is prevented from being securely adhered to the surface. In the case of the sheets with linered parts, it is frequently difficult to separate the liner edge from the sheet so that the liner can be grasped for removal. Peeling away of the liners must be done as a separate step prior to application of the sheets to receptor surfaces, and liner removal frequently results in contacting the adhesive coating with one's fingers which contaminates the adhesive and inhibits its ability to adhere to a surface.

SUMMARY OF THE INVENTION

In its simplest form, the present invention comprises a single, flexible, pressure-sensitive adhesive coated sheet having one or more co-terminal folded V-shaped tabs attached to at least a portion of the adhesive coated surface. In this invention, one leg of the V-fold tab is adhered to the adhesive coated side of the sheet. The unattached leg of the tab forms a handle which is easily grasped to facilitate manual separation of the tab from the sheet when it is adhered to a receptor surface. When a sheet is applied to a receptor surface, the distal end of the sheet is applied to the surface while the user grasps the unattached leg of the V-fold tab and separates the attached leg of the tab from the sheet without contacting the adhesive coating so that the sheet will securely adhere to the surface.

Another aspect of the invention involves a pad formed from a plurality of the aforementioned sheets with each sheet having a single tab adhered to it. A useful feature of co-terminal, V-fold tabs for this application is their tendency to "self-fan", thus making it easier for the user to grasp the tab on the top sheet and separate the sheet from the pad. The V-fold tab configuration also enables the user to pull the tab away from the adhesive layer without contacting the adhesive as the tabbed end of the sheet is pressed into contact with the receptor surface.

This ease of application is an attractive feature when the sheets are comprised of medical tape. As is often the case when one is tending to a wound on one's own hand, arm, or back, it is inconvenient or impossible to use two hands in applying the tape to the wound. The present invention provides the user with an improved medical tape and a convenient method of applying the tape to a wound using only one hand.

It is also a feature of this invention to provide a sheet with a sterile absorbent pad located in a center portion of the sheet with a V-fold tab positioned at each end of the sheet. This positioning would allow a user to apply the sheet without contacting the sterile pad.

The present invention may include adhesive coated sheets of many different types intended for many different uses. Examples of some uses are transparent adhesively coated sheets adapted to overlay and protect surfaces from moisture and abrasion such as shipping labels, sheets having adhesive coated only in a band around their peripheries used to attach packing slips to packages, and porous, adhesively coated sheets of the type adapted to be adhered over injuries or incisions in the human body.

BRIEF DESCRIPTION OF THE DRAWINGS

The present invention will be more thoroughly understood by reference to the accompanying drawings where like numbers refer to like parts in the several views, and wherein.

DETAILED DESCRIPTION

Figure 1:
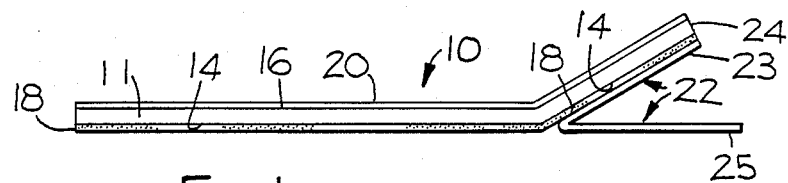
FIG. 1 is a side view of a single pressure-sensitive adhesive coated sheet with a tab according to the present invention.
Figure 3:
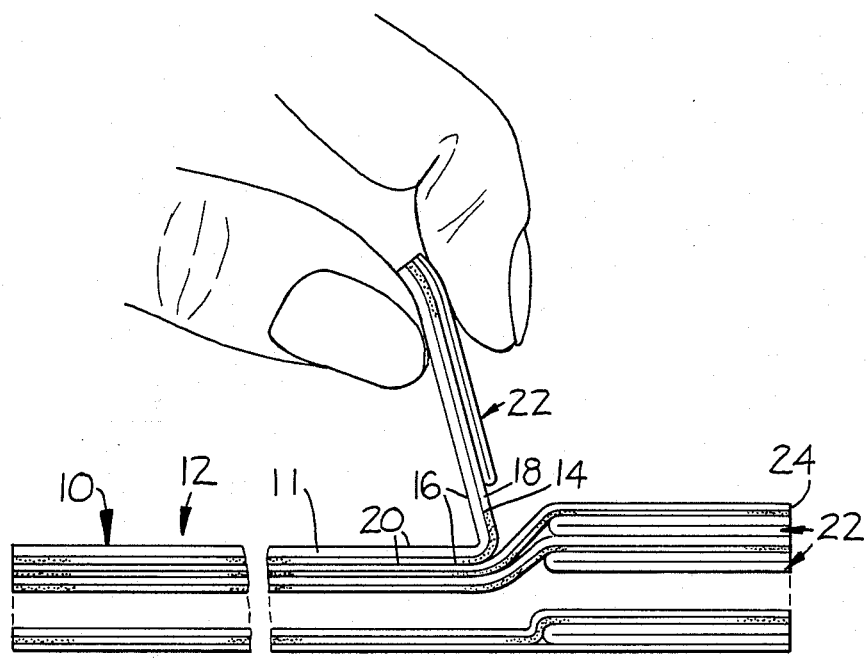
FIG. 3 is an enlarged side view illustrating a sheet being separated from the pad shown in FIG. 2.

Referring now to the drawings, there is shown in FIG. 1 a single pressure-sensitive adhesive coated sheet according to the present invention, generally designated by the reference numeral 10. The sheet 10 comprises a backing member 11 having first and second opposite surfaces 14 and 16. There is a pressure-sensitive adhesive coating 18 on the first surface 14 and a low adhesion backsize coating 20 on the second surface 16. (The backsize coating 20 is magnified in FIG. 1 for illustrative purposes and is shown as a layer, but in selected subsequent views it is not shown as a separate layer.) At one end of sheet 10, V-fold tab 22 has one leg 23 attached to the coating 18 and has a second leg 25 extending freely. The V-fold tab 22 provides an area that is easily grasped by the user when pulling the sheet 10 from a pad of stacked sheets (as shown in FIG. 3).

Figure 2:
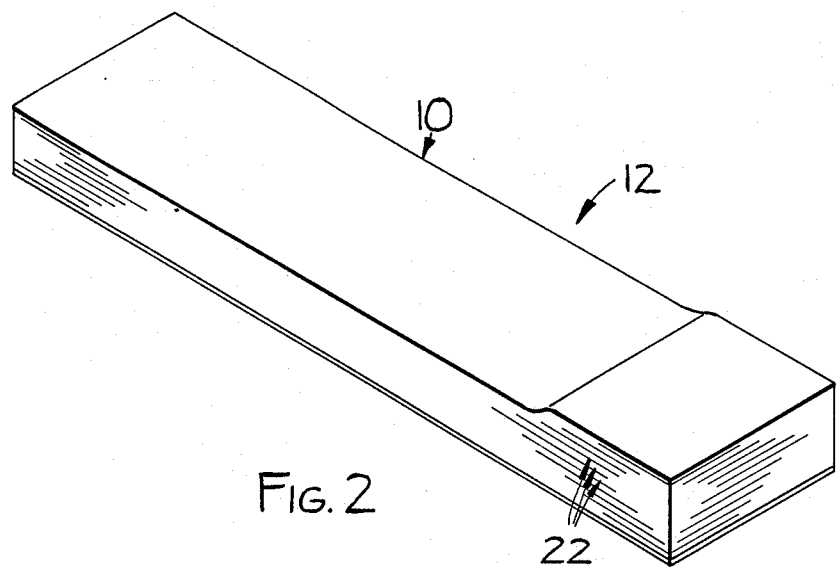
FIG. 2 is a perspective view of a plurality of sheets forming a tape pad according to the present invention.

FIG. 2 shows a tape pad 12 comprised of a plurality of sheets 10 of the same shape and size stacked one upon another. FIG. 3 shows each sheet 10 comprising a backing member 11 having first and second opposite surfaces 14 and 16, a pressure-sensitive adhesive coating 18 on first surface 14, and a low adhesion backsize coating 20 on its second surface 16. Each sheet 10 is adapted to be adhered to a surface. V-fold tab 22 has first leg 23 adhered to the adhesive coating 18 and second leg 25 extending freely. Legs 23 and 25 are identically sized and extend to a corresponding peripheral edge 24 of sheet 10 in a co-terminal relationship. The sheets 10 are disposed with their peripheries generally aligned and with first and second surfaces 14 and 16 of adjacent sheets 10 juxtaposed and adhered to each other by adhesive coating 18; the self-fanning, co-terminal, V-fold tabs 22 separate sheets 10 thus facilitating separation of individual sheets 10 from the rest of the pad 12.

The co-terminal, V-fold tabs 22 are formed from a seamless tube of 0.05 mm wall thickness polymeric material, preferably a pigmented, low density polyethylene. The surface energy of the polyethylene is important since the 90° peel adhesion of the V-tab/adhesive interface (shown as 29 in FIG. 4) must allow smooth removal of the tab 22 during peeling without removing the adhesive 18 from the backing 11. Therefore, the adhesion of the sheet/adhesive interface must be greater than that of the tab/adhesive interface.

In the pad embodiment, the surface energies and roughness of the inner walls of the polyethylene tube are important factors and must be controlled to overcome the tendency of the tabs to "block" (stick to each other) after the pads have been subjected to the high pressure shearing action of the die cutting process utilized in forming the V-fold tabs. Polyethylene tubing is often corona treated to increase its receptivity to most types of printing ink. Such treatment increases the surface energy of the polyethylene resulting in high adhesion values at the tab/adhesive interface and consequent removal of adhesive 18 from the backing 11 when the V-fold tab 22 is removed therefrom. Accordingly, non-corona treated polyethylene tubing is preferred to make the V-fold tabs 22 of the present invention.

The surface energy of the tube may be selectively controlled (through chemical or radiative priming) to maintain the above described relationship for a broad range of adhesive/sheet surface energies dictated by the intended end uses.

The 90° peel adhesion of the V-fold tab 22 from the tape adhesive 18 should be in the range of 16–30 grams per centimeter as determined by ASTM method D 1876–72 (reapproved 1983). Upon accelerated aging, 11 days at 49° C., the 90° peel adhesion should not exceed 90 grams, and preferably should be in the range of 40–55 grams per centimeter. When corona treated high density polyethylene tube is used for the V-fold tab, the 90° peel adhesion can rise to 40–87 grams per centimeter.

For single sheets, the thickness of the tubing can vary widely and is preferably greater than 0.025 mm; however, in the pad embodiment when the tube wall thickness exceeds 0.075 mm, the tab stack becomes excessively thick which unduly limits the number of sheets in the pad. If the tube wall thickness is less than 0.025 mm, the tubing is easily over-stretched during attachment to the pressure-sensitive adhesive of the sheet stock which produces excessive curl of the tab ends and excessive self-fanning of the tab stack.

Figure 4:
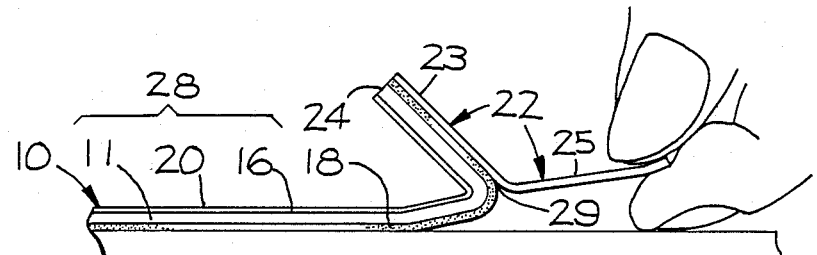
FIG. 4 is a side view of a single sheet being applied to a substrate with a co-terminal, V-fold tab being pulled away with the relationships of the interfaces between the tab and pressure-sensitive adhesive layer, and between the pressure-sensitive adhesive layer and sheet material being clearly visible.

The sheet 10 is intended to be applied to a substrate as illustrated in FIG. 4. Major portion 28 is initially contacted and adhered to substrate 30. The unattached leg 25 is then grasped and pulled in a direction away from major portion 28 of the sheet 10. As the attached leg 23 is progressively separated from the adhesive 18, the newly exposed adhesive portion of the sheet 10 contacts the substrate 30. This occurs simultaneously until the sheet 10 is in complete contact with the substrate 30. The adhesive surface 18 of the sheet 10, therefore never contacts the user's fingers, thus remaining uncontaminated.

Figure 7:
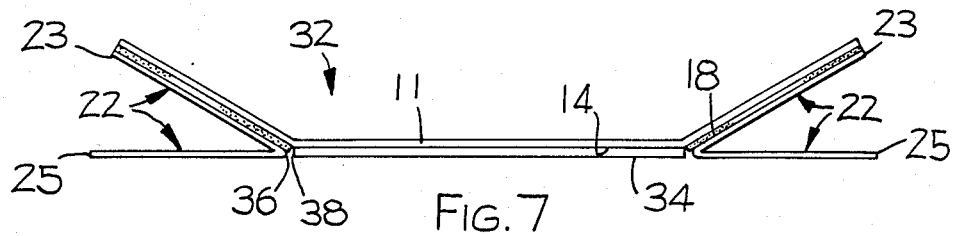
FIG. 7 is a side view of a single sheet with centrally positioned sterile absorbent pad and V-fold tabs located at each end.

A further embodiment of the present invention is shown in FIG. 7. Sheet 32 comprises a backing 11 having a first surface 14. First surface 14 has a layer of pressure-sensitive adhesive 18 thereon. At each end of sheet 32, there is a V-fold tab 22. V-fold tabs 22 have legs 23 and 25. Legs 23 are attached to coating 18 while legs 25 extend freely. Sterile pad 34 is located in a center portion of sheet 32 with each folded edge portion 36 of the V-fold tabs 22 extending to an edge portion 38 of sterile pad 34. Folded edge portion 36 of the V-fold tabs 22 may also extend substantially to the center of the sterile pad 34 thus covering and protecting the sterile pad 34 from contamination.

Figure 5:
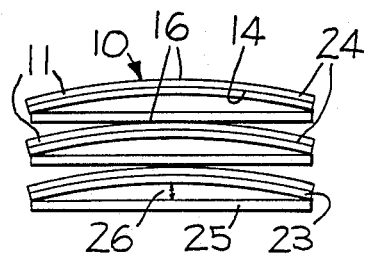
FIG. 5 is an end view of the tape pad.
Figure 6:
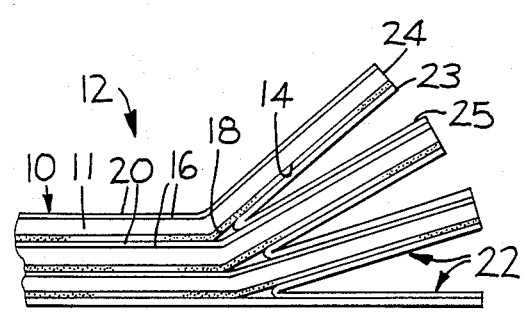
FIG. 6 is a side view of the tape pad showing the "self-fanning" tendency of the V-fold tabs.

The curl or "cupping" of the tab ends shown in FIG. 5 further results in self-fanning of the tabs (shown in FIG. 6) and facilitates the ease with which the tabs 22 may be grasped with the fingers. This curl is caused by relaxation of tension in the tab material (tubing). The curl is measured by attaching a die cut tape strip to a flat surface and measuring the height of the arch at the midpoint using a ruler or optical comparator, (the distance 26 in FIG. 5). The extent of curl, quantified by distance 26, is a function of many variables; some of these variables include tab length and width, the tension of the tubing at the time it is applied to the pressure-sensitive adhesive of the sheet, the differential in elasticity of the tab and sheet materials, and environmental conditions such as temperature and humidity. With these factors in mind, the distance 26 can be controlled through judicious choice of the design (tab length), process (tension), and materials (elasticity) parameters.

The invention is further illustrated by the following examples.

EXAMPLE 1

A single pressure-sensitive adhesive coated tabbed sheet of medical tape was made using a non-woven, substantially inextensible microporous medical tape (Micropore brand surgical tape available from 3M Company) as the sheet material. Micropore brand surgical tape is fully described in U.S. Pat. No. 3,121,021. The tabs were formed from low density polyethylene tubing (Rexene polyethylene PE109 Tube available from El Paso Products Company). This tubing is 3.75 cm wide and has a wall thickness of 0.05 mm. The tube was colored with pellets of CB Edwards #CBE 21797 E blue color concentrate available from CB Edwards Company.

The 90° peel adhesion of the V-fold tab from the adhesive of the tape backing was 19 grams per cm as measured by ASTM D 1876-72. After accelerated aging for 11 days at 49° C., the peel adhesion of the V-fold tab was 32 grams per cm as measured by ASTM D 1876-72.

EXAMPLE 2

Example 1 was repeated using a bandage tape made from a spun-bond, non-woven polyester fabric available from E. I. duPont de Nemours Co. Inc. under the name Sontara. The resulting tabbed sheet had acceptable adhesion strength pursuant to this invention.

EXAMPLE 3

Example 1 was repeated using a woven cloth tape with an adhesive coating weight of 6.7 milligrams per $cm^2$ (Durapore brand surgical tape from 3M Company) as the sheet material. The 90° peel adhesion of the V-fold tab from the adhesive was 21 grams per cm as measured by ASTM D 1876-72.

EXAMPLE 4

Example 1 was repeated using a knit sheet material (Tricot Mesh bandage, available from Johnson & Johnson Products Inc.). The 90° peel adhesion of the V-fold tab from the adhesive of the bandage was 64 grams per cm as measured by ASTM D 1876-72.

EXAMPLE 5

A number of first-aid bandage strips with two co-terminal, V-fold tabs were made from a single master sheet of surgical tape (Micropore brand surgical tape of Example 1) measuring 33×10 cm. Twelve (12) non-stick, adsorbent pads 2.5×2.2 cm were positioned on the center line of the tape master sheet. The pads were spaced 0.3 cm from one another and attached to the master sheet by pressing them into contact with the adhesive coating. The pads were of the non-stick variety (3M Brand Non-Stick Pad, available from 3M Company). The non-stick pads are more completely described in U.S. Pat. No. 3,285,245. A 33 cm length of 5 cm wide, 0.0375 mm thick blue Rexene tubing available from El Paso Products Co. was attached to each end of the sheets with the folded edges of the tubing in contact with the edge of the adsorbent pads. A rule die was positioned over the pad with a 1.5 millimeter space between the edge of a pad and the sides of the die. Twelve (12) first-aid bandage strips measuring 7.6×2.5 cm were cut from the master sheet with the rule die. The resulting sheet applied easily to a wound without any contamination of the absorbent pad.

EXAMPLE 6

Example 6 was repeated using a bandage tape made from a spun-bond, non-woven polyester fabric available from E. I. duPont de Nemours Co. Inc. under the trade name Sontara in place of Micropore brand surgical tape. The resulting sheet applied easily to a wound without any contamination of the absorbent pad.

Although the present invention has been described with reference to specific embodiments thereof, it will be appreciated by those skilled in the art that many modifications can be made in the tape strips and pads of the present invention without departing from the spirit of the invention. For example, the sheets may be of any suitable transparent, translucent, or opaque flexible material. The adhesive coating may extend over all or only a part of the sheets. The V-fold tabs may or may not all be of the same size, may be disposed at different relative locations on various sheets in the pad, and may cover a major portion of the sheet adhesive surface. One specific example of such a variant is the placing of V-fold tabs at different ends of the pad on alternate sheets. In the first-aid bandage strips, the V-fold tabs may be configured so that the leading edges of the freely hanging legs may overlap each other thereby completely covering the absorbent pad.

What is claimed is:

1. A single, flexible sheet comprising a backing having first and second surfaces; a coating of pressure-sensitive adhesive on the first surface of said backing; a folded liner strip forming a V-fold tab wherein the V-fold tab is prepared from polymeric tubing, one leg of said tab adhered to said pressure-sensitive adhesive on a portion of said backing, said tab extending to and coterminous with the peripheral edges of said sheet portion; the unattached leg of said tab hanging freely and forming a handle to facilitate manual separation of said tab from the sheet as the tab covered portion of said sheet is urged into contact with a receptor surface; said handle being identical in dimensions with said attached leg of said tab.

2. The sheet of claim 1 wherein the polymeric tubing is low density polyethylene.

3. The sheet of claim 1 wherein the polymeric tubing is comprised of high density polyethylene.

4. The sheet of claim 1 wherein the backing is a medical tape.

5. The sheet of claim 4 wherein the medical tape is woven or knitted fabric.

6. The sheet of claim 5 wherein the medical tape is non-woven fabric.

7. The sheet of claim 1 wherein the V-fold tab covers a major portion of the adhesive coated sheet surface.

8. The sheet of claim 1 having two V-fold tabs, said tabs being attached at opposite ends of the sheet.

9. A first-aid bandage strip comprising the flexible sheet of claim 1; a sterile, absorbent pad adhered to the center portion of the backing; and a folded liner strip at each end of the bandage strip.

10. A tape pad comprising a plurality of stacked, flexible sheets of claim 1; the sheets being adhered to one another with the first adhesive coated surface adhering to the second surface of an adjacent sheet; said folded liner strips separating portions of said stacked sheets and forming a handle to facilitate manual separation of the top sheet from the underlying sheets in the pad.

11. A tape pad according to claim 10 wherein the liner strips position the linered portions of the sheets away from each other thereby creating self-fanning V-fold tabs.

12. A tape pad according to claim 10 wherein said V-fold tabs are attached at opposite ends of adjacent sheets.

13. A tape pad according to claim 10 wherein said V-fold tabs cover a major portion of the adhesive coated surface of said backing.

14. A tape pad according to claim 10 wherein said V-fold tabs cover a minor portion of the adhesive coated surface of said backing.

* * * * *